(12) United States Patent
Tholen et al.

(10) Patent No.: US 6,351,675 B1
(45) Date of Patent: Feb. 26, 2002

(54) SYSTEM AND METHOD OF PROGRAMMING AN IMPLANTABLE MEDICAL DEVICE

(75) Inventors: Astrid M Tholen, Houten; Geeske Van Oort, Nieuwleusen, both of (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/677,980

(22) Filed: Oct. 3, 2000

Related U.S. Application Data
(60) Provisional application No. 60/157,131, filed on Oct. 4, 1999.

(51) Int. Cl.[7] ............................................. A61N 1/362
(52) U.S. Cl. ....................................................... 607/59
(58) Field of Search ..................................... 607/30, 59

(56) References Cited

U.S. PATENT DOCUMENTS

| | | |
|---|---|---|
| 3,660,753 A | 5/1972 | Judd et al. |
| 4,194,147 A | 3/1980 | Payne et al. |
| D314,732 S | 2/1991 | Weder .................. D11/143 X |
| D365,305 S | 12/1995 | Weder et al. .......... D11/143 X |
| D366,009 S | 1/1996 | Weder et al. .......... D11/143 X |
| D366,631 S | 1/1996 | Weder et al. .......... D11/152 X |
| 5,617,016 A | 4/1997 | Borghi et al. |
| 5,731,694 A | 3/1998 | Wilcox et al. |
| 5,734,259 A | 3/1998 | Sisson et al. |
| 5,770,940 A | 6/1998 | Goder |
| 5,886,508 A | 3/1999 | Jutras |
| 5,917,313 A | 6/1999 | Callahan, Jr. |
| 5,949,222 A | 9/1999 | Buono |
| 5,982,161 A | 11/1999 | Nguyen et al. |

OTHER PUBLICATIONS

International IR Rectifier, "Radiation Hardened Power MOSFET Thru–Hole (MO–036AB)," IRHG6110, 100V, Combination 2N–2P–Channel, RAD–Hard HEXFET, MOSFET Technology, pp. 1–14, (Mar. 2000).

Motorola Inc., "Switchmode Power Supplies," *Reference Manual and Design Guide*, pp. 1–136, (May 1999).

Texas Instruments Incorporated, "Analog and Mixed Signal Products," Analog Application Journal, pp. ii–29, (Nov. 1999).

Watkins, Steve, "History and Development of Switched-Mode Power Supplies Pre 1987," pp. 21, 1987, 1998).

*Primary Examiner*—Scott M. Getzow
(74) *Attorney, Agent, or Firm*—Thomas F. Woods; Thomas G. Berry

(57) ABSTRACT

A system and method of programming an implantable medical device is disclosed. The system includes a causal model coupled to an implantable medical device and capable of identifying at least one cause of an abnormal condition associated with the implantable medical device or the patient. An abductive inference engine is coupled to the causal model and is capable of identifying a suggested updated setting for the implantable medical device to alleviate the abnormal condition. A display is coupled to the causal model and displays the abnormal behavior and the suggested updated settings to the clinician such that the clinician may implement the suggested updated settings.

64 Claims, 12 Drawing Sheets

| Expert conclusion | Total n | Correct n | Incorrect n | Unclassified n |
|---|---|---|---|---|
| Far Field R wave sensing, and P amplitude low | 1 | 0 | 1 | 0 |
| Far Field R wave sensing | 10 | 8 | 0 | 2 |
| P-wave amplitude low | 5 | 5 | 0 | 0 |
| Retrogade conduction | 3 | 2 | 0 | 1 |
| Total | 19 | 15 | 1 | 3 |

*FIG. 13*

| System conclusion | Total n | Correct n | Incorrect n |
|---|---|---|---|
| Far Field R wave sensing | 9 | 8 | 0 |
| P-wave amplitude low | 5 | 5 | 0 |
| Retrogade conduction | 2 | 2 | 0 |
| Total | 16 | 15 | 1 |

*FIG. 14*

SYSTEM AND METHOD OF PROGRAMMING AN IMPLANTABLE MEDICAL DEVICE

This application claims benefit to Provisional Application No. 60/157,131 filed Oct. 4, 1999.

THE FIELD OF THE INVENTION

The present invention relates generally to a system and method used in conjunction with an implantable medical device. More specifically, the present invention relates to a system and method of providing programming information relating to an implantable medical device based upon an abductive diagnostic reasoning strategy.

BACKGROUND OF THE INVENTION

Cardiac disease affects millions of people throughout the world. Cardiac disease may cause the excitatory and conductive system of the heart to fail, resulting in an abnormal cardiac rhythm, usually referred to as arrhythmia. Some arrhythmias are very dangerous, and may lead to death of the patient. Other arrhythmias may be the origin of less threatening conditions, but for which medical treatment is nevertheless required. One of the possible treatments for patients is assistance by an implantable medical device (IMD).

Modern IMDs, such as pacemakers or defibrillators, are complicated electronic devices, capable of providing assistance on demand, i.e., when the excitatory and conductive system of the heart fails to operate normally. In order to accommodate specific patient needs, an IMD may be programmed by setting particular parameters such that the resulting therapy is optimal for the patient.

Overall IMD systems known in the art comprise several components, including an IMD, pacing and/or sensing leads, and a programmer. The leads connect the IMD to the heart of a patient. The IMD stores a variety of different types of diagnostic data which assist a clinician in evaluating both the operation of the heart of the patient and the operation of the IMD. The specific diagnostic data stored by the IMD includes a variety of information, including a real-time event recording of pacing events.

The programmer of the overall IMD system is a microprocessor-based device, which is a stand-alone unit commonly located at a hospital or within a clinician's office. To utilize the programmer, it is positioned in proximity to the IMD. The programmer is capable of communicating with the IMD and displaying information on a display screen. Depending upon the specific programmer, the programmer may be capable of reading information from and transmitting information to the IMD. Other programmers are only capable of monitoring or receiving information from the IMD, without the capability of transmitting information to the IMD. The programmer of the overall IMD system provides multiple functions, including assessing lead performance during a pacemaker or a defibrillator implantation, receiving feedback information from the IMD for use by the clinician, and, depending upon the specific programmer, programming the IMD.

An analyzer, which is sometimes a sub-component of the programmer and sometimes an individual component, is also a microprocessor-based device. The analyzer assists the clinician in assessing the electrical performance of a pacing lead system used in conjunction with an IMD system. The analyzer utilizes the programmer as a control and display platform.

There are numerous instances in which diagnostic data must be monitored during an adjustment procedure or must be retrieved from the IMD and displayed on the display screen of the programmer. For example, during a routine visit of the patient to a clinic, it is often necessary to retrieve information related to the IMD or the patient. Second, during a visit to a clinic, a clinician may want to perform a series of tests on the patient and view a variety of information related to the IMD and the patient. Third, during a medical procedure on the patient unrelated to the IMD, it may be necessary to monitor and/or adjust various parameters of the IMD prior to the medical procedure to ensure adequate performance of the IMD during the unrelated medical procedure.

An IMD and a programmer communicate with each other by means of an inductive transreceiver coil located within the programmer and an inductive transreceiver coil located within the IMD. In addition, the IMD includes a programmer detection system which detects the presence of a programmer in proximity to the IMD. For example, the programmer detection system is in a first state when a programmer is not proximal to the IMD. However, when a programmer is proximal to the IMD, the programmer detection system changes from the first state to a second state. With the programmer detection system in the second state, indicating the presence of a programmer proximal to the IMD, a communication system within the IMD is permitted to communicate with the programmer via the inductive transreceiver coils.

Unfortunately, reprogramming an IMD is not an easy task. Both sufficient time and knowledge of various IMD therapies must be available. In many patients, specific IMD therapy is sub-optimal due to a lack of one or both of these factors. In many situations, the original factory settings for an IMD are kept unchanged. On the one hand, technology relating to IMDs is moving fast, and the role of software programming is increasing, yielding IMDs that are constantly enhanced in their capabilities. On the other hand, there are limitations of what clinicians can and are willing to do with respect to customizing settings of an IMD for a particular patient. They are beginning to realize that some form of intelligent decision support is needed in order to permit patients to benefit from further advances in IMD technology.

The patents listed in Table 1 are examples of different systems and methods, which attempt to aid a clinician in accessing the efficiency of an IMD with respect to a specific patient.

TABLE 1

| U.S. Pat. No. | Inventor | Issue Date |
| --- | --- | --- |
| 5,722,000 | Snell | March 3, 1998 |
| 5,716,384 | Snell | Feb. 10, 1998 |
| 5,716,382 | Snell | Feb. 10, 1998 |
| 5,713,938 | Chiang et al. | Feb. 3, 1998 |
| 5,711,297 | Iliff | Jan. 27, 1998 |
| 5,704,366 | Tacklind et al. | Jan. 6, 1998 |
| 5,660,183 | Chiang et al. | Aug. 26, 1997 |
| 5,660,176 | Iliff | Aug. 26, 1997 |
| 5,619,991 | Sloane | April 15, 1997 |
| 5,615,112 | Liu Sheng et al. | March 25, 1997 |
| 5,594,638 | Iliff | Jan. 14, 1997 |
| 5,517,405 | McAndrew et al. | May 14, 1996 |
| 5,447,164 | Shaya et al. | Sept. 5, 1995 |

All patents listed in Table 1 above are hereby incorporated by reference herein in their respective entireties. As those or ordinary skill in the art will appreciate readily upon reading the Summary of the Invention, Detailed Description of the Preferred Embodiments, and claims set forth below, many of the devices and methods disclosed in the patents of Table 1 may be modified advantageously by using the teachings of the present invention.

One disadvantage of prior art systems, including those listed in Table 1, relates to the inefficiency of the systems to properly provide programming/reprogramming information relating to relevant tests to be performed for further evaluation of an IMD or relating to optimal settings for a specific IMD implanted in a specific patient. Another disadvantage of prior art systems is the inability to provide a structured, systematic approach to identifying proper IMD setting and the inability to prompt a clinician to perform addition test or analysis.

Therefore, there is a continuing need for a system and method which provides a clinician with information relating to an IMD and a patient such that the clinician can quickly and easily identify additional relevant tests or provide the optimal setting for IMD therapy.

SUMMARY OF THE INVENTION

The present invention overcomes the disadvantages of the prior art by providing a method of and a system for providing programming information relating to an implantable medical device based upon an abductive diagnostic reasoning strategy.

The present invention has certain objects. That is, the present invention provides solutions to certain problems existing in the prior art such as: (a) an inability to identify at least one cause of an abnormal condition relating to an implantable medical device; (b) an inability to provide optimal programming information relating to an implantable medical device; (c) an inability to utilize an abductive diagnostic reasoning strategy to provide optimal programming information for an implantable medical device; (d) an inability to provide a systematic method capable of evolving based upon previous determined information, resulting in the determination of optimal programming information relating to an implantable medical device;(e) an inability to categorize information relating to an abnormal condition associated with the implantable medical device or a patient into one of three solution categories: rejected solutions, suspected solutions, or confirmed solutions; (f) an inability to compare observed findings relating to an abnormal condition to predicted findings based upon a model of abnormal behavior; and (g) an inability to display abnormal conditions associated with an implantable medical device and display suggested updated settings for the implantable medical device.

The system and method of the present invention provides certain advantages, including: (a) the ability to identify at least one cause of an abnormal condition relating to an implantable medical device; (b) the ability to provide optimal programming information relating to an implantable medical device; (c) the ability to utilize an abductive diagnostic reasoning strategy to provide optimal programming information for an implantable medical device; (d) the ability to provide a systematic method capable of evolving based upon previous determined information, resulting in the determination of optimal programming information relating to an implantable medical device;(e) the ability to categorize information relating to an abnormal condition associated with the implantable medical device or a patient into one of three solution categories: rejected solutions, suspected solutions, or confirmed solutions; (f) the ability to compare observed findings relating to an abnormal condition to predicted findings based upon a model of abnormal behavior; and (g) the ability to display abnormal conditions associated with an implantable medical device and display suggested updated settings for the implantable medical device.

The system and method of the present invention has certain features, including a model of abnormal conditions used as a basis for determining optimal settings for a particular implantable medical device in conjunction with a specific patient. The model of abnormal conditions provides that predicted abnormal findings with may be compared to actual observed findings associated with an implantable medical device. A causal model is capable of identifying at least one cause of an abnormal condition, while an abductive inference engine is capable of identifying suggested updated settings for the implantable medical device in response to the abnormal conditions.

BRIEF DESCRIPTION OF THE DRAWINGS

FIG. 13 is a table illustrating results of an expert compared to results of the system of the present invention.

FIG. 14 is a table illustrating results by comparing diagnoses produced by an expert with those results produced by the system of the present invention.

DESCRIPTION OF THE PREFERRED EMBODIMENTS

In the following detailed description of the preferred embodiments, reference is made to the accompanying drawings that form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

FIGS. 1–5 and associated text provide a detailed understanding of the inner-workings of an implantable medical device ("IMD"), as well as a general understanding of the interconnection of an IMD to a heart of a patient. FIGS. 6–14 and associated text provide a detailed understanding of a system and method of providing programming information relating to an IMD based upon an abductive diagnostic reasoning strategy in accordance with the present invention.

Figure 1:
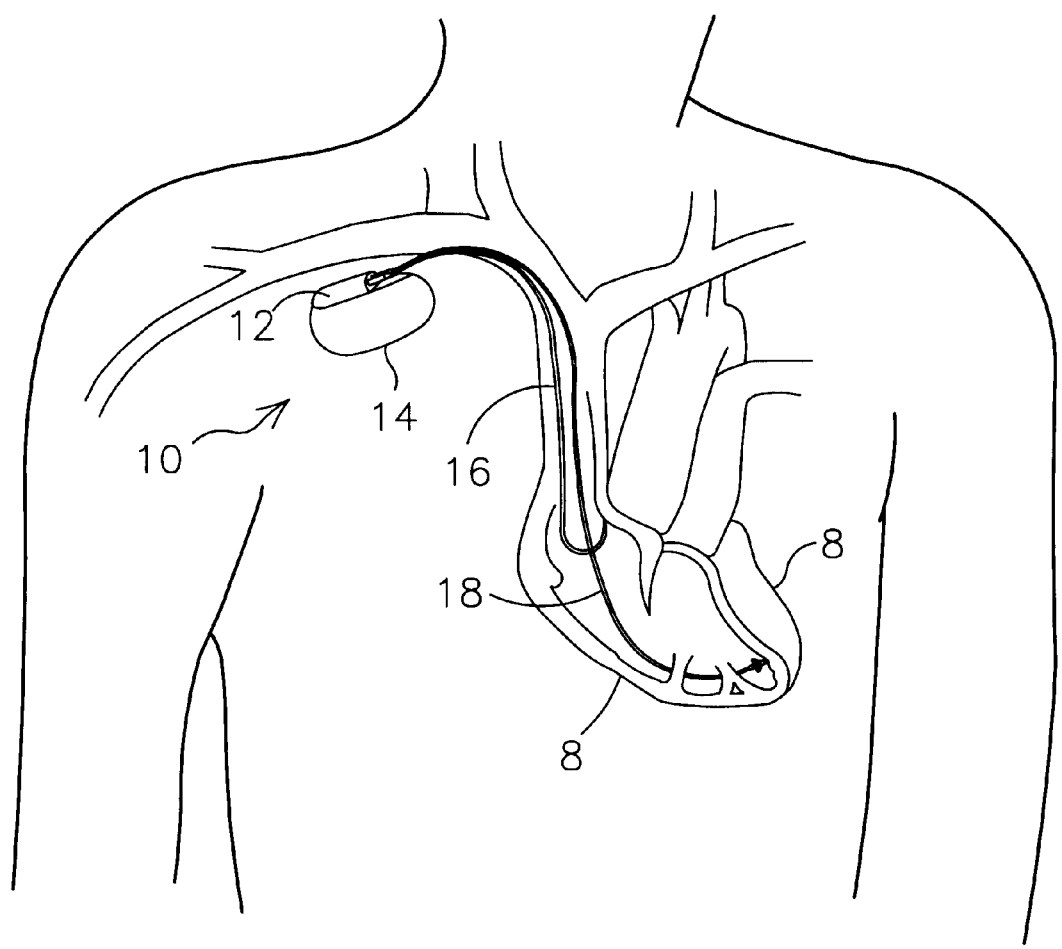
FIG. 1 is a simplified schematic view of one embodiment of an implantable medical device.

FIG. 1 is a simplified schematic view of one embodiment of IMD 10 of the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 2:
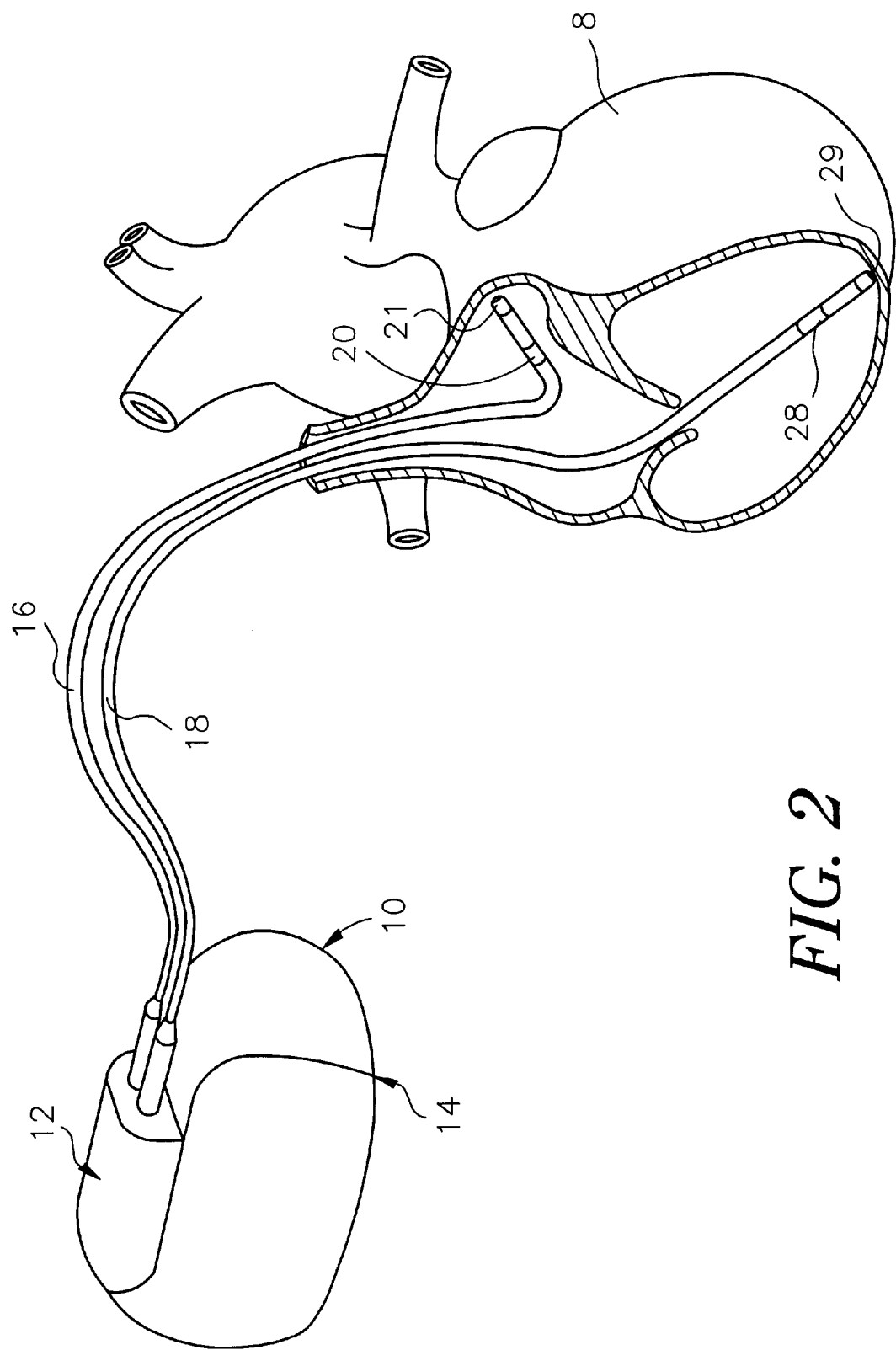
FIG. 2 is a simplified illustration of an implantable medical device with leads positioned within passageways of a heart.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
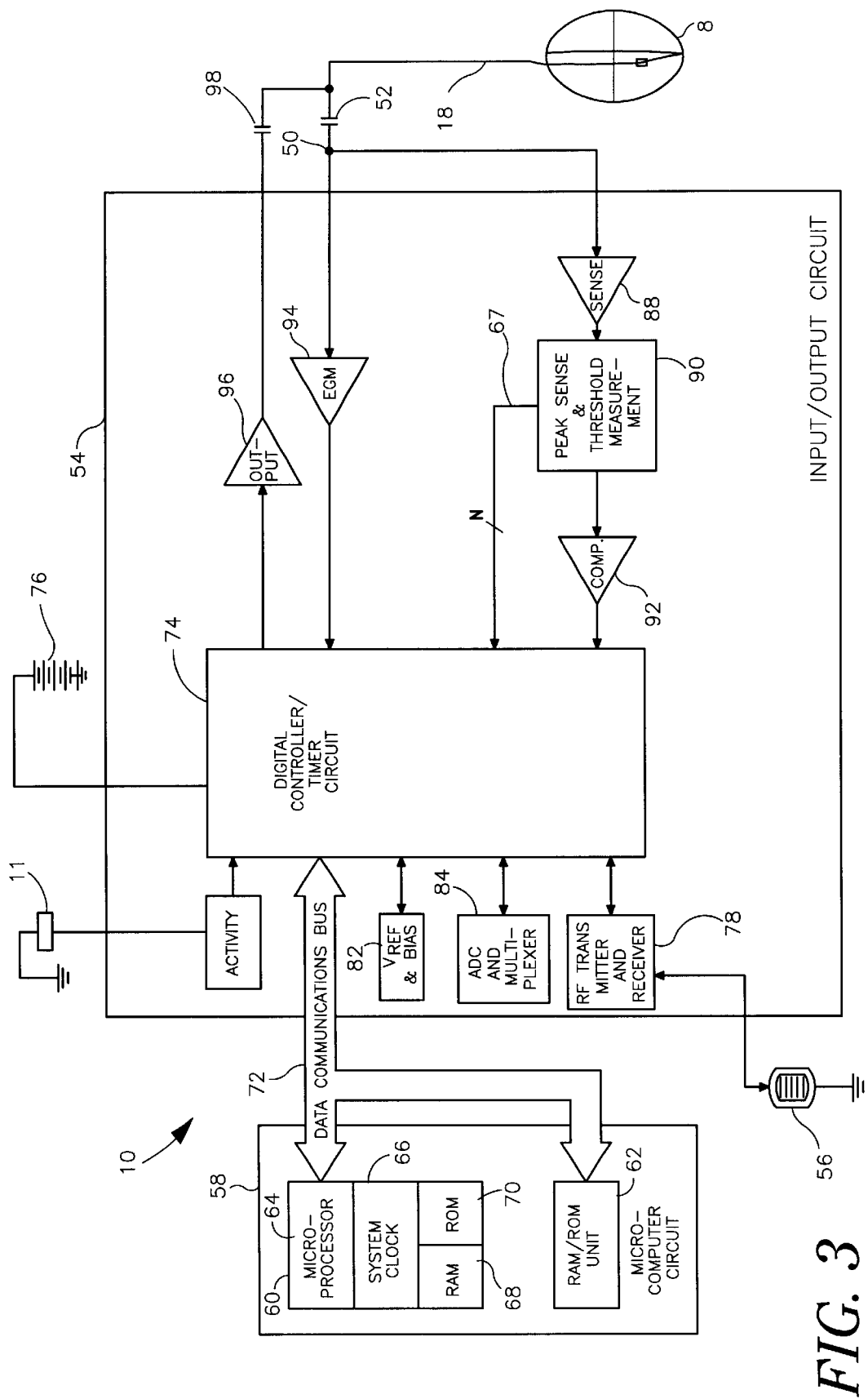
FIG. 3 is a block diagram illustrating the constituent components of an implantable medical device.

FIG. 3 shows a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

Figure 11:
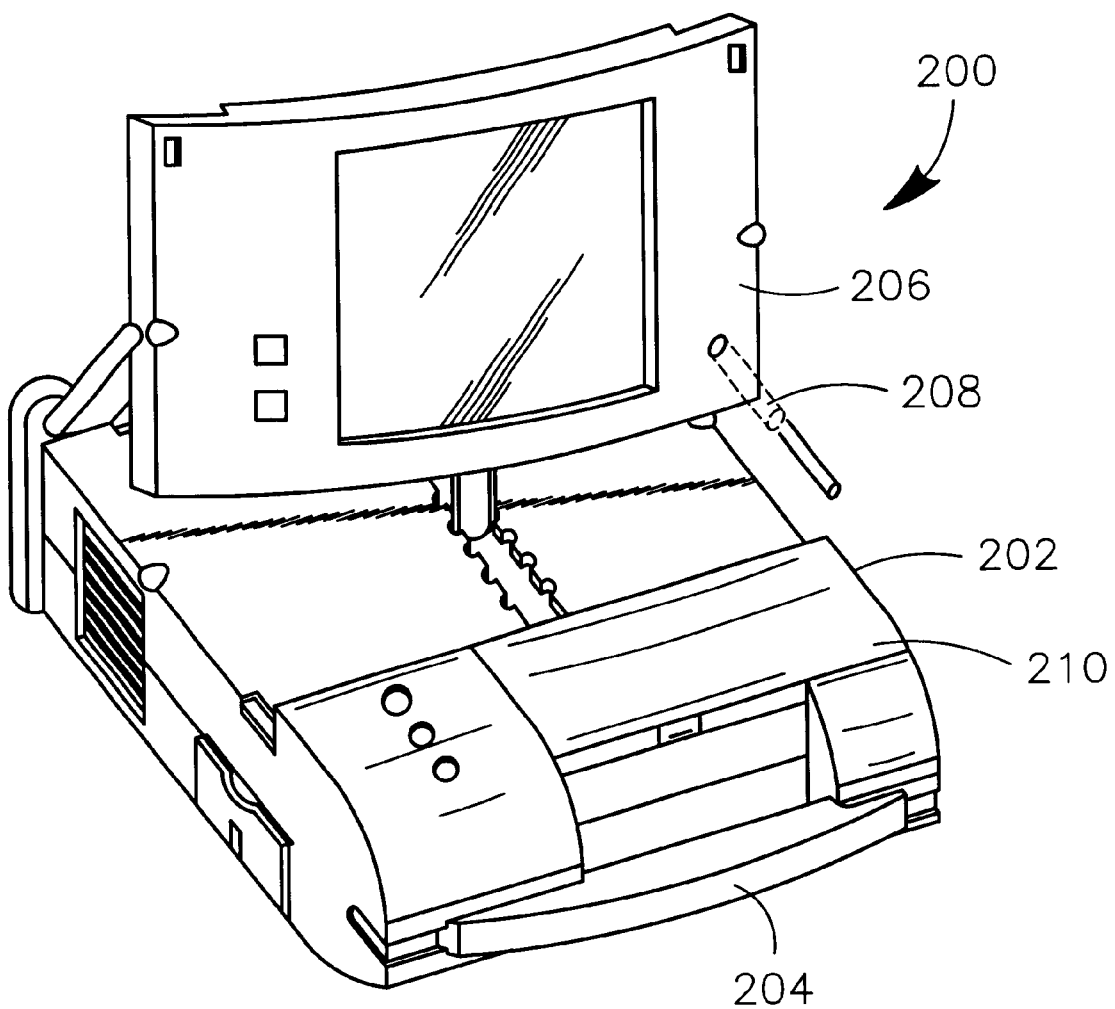
FIG. 11 is a perspective view of a programmer unit used in conjunction with an implantable medical device.

IMD 10 in FIG. 3 is most preferably programmable by means of an external programming unit (shown in FIG. 11). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all hereby incorporated by reference herein, each in its respective entirety.

Figure 4:
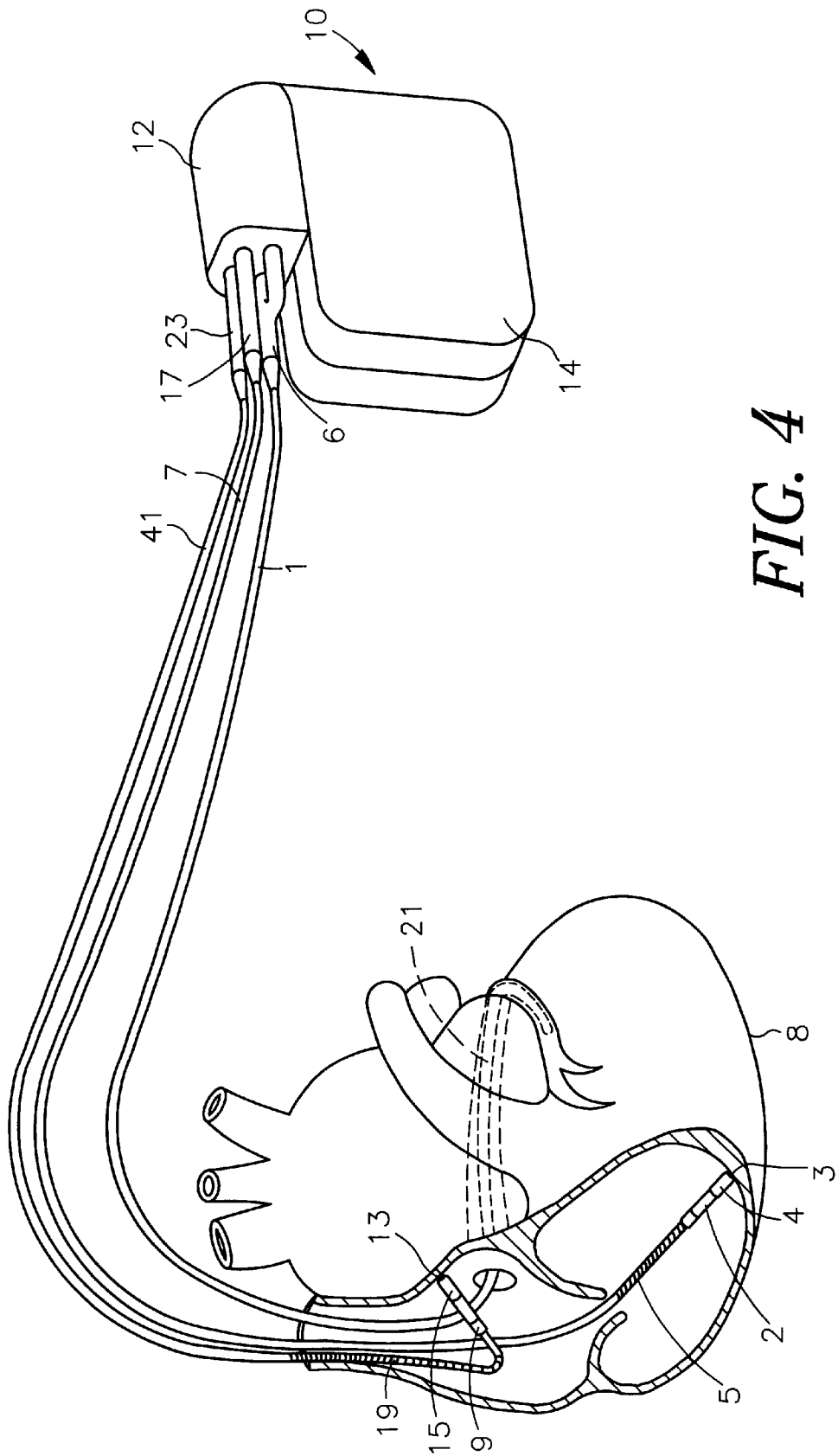
FIG. 4 is a simplified schematic view of an implantable medical device with leads positioned within passageways of a heart.
Figure 5:
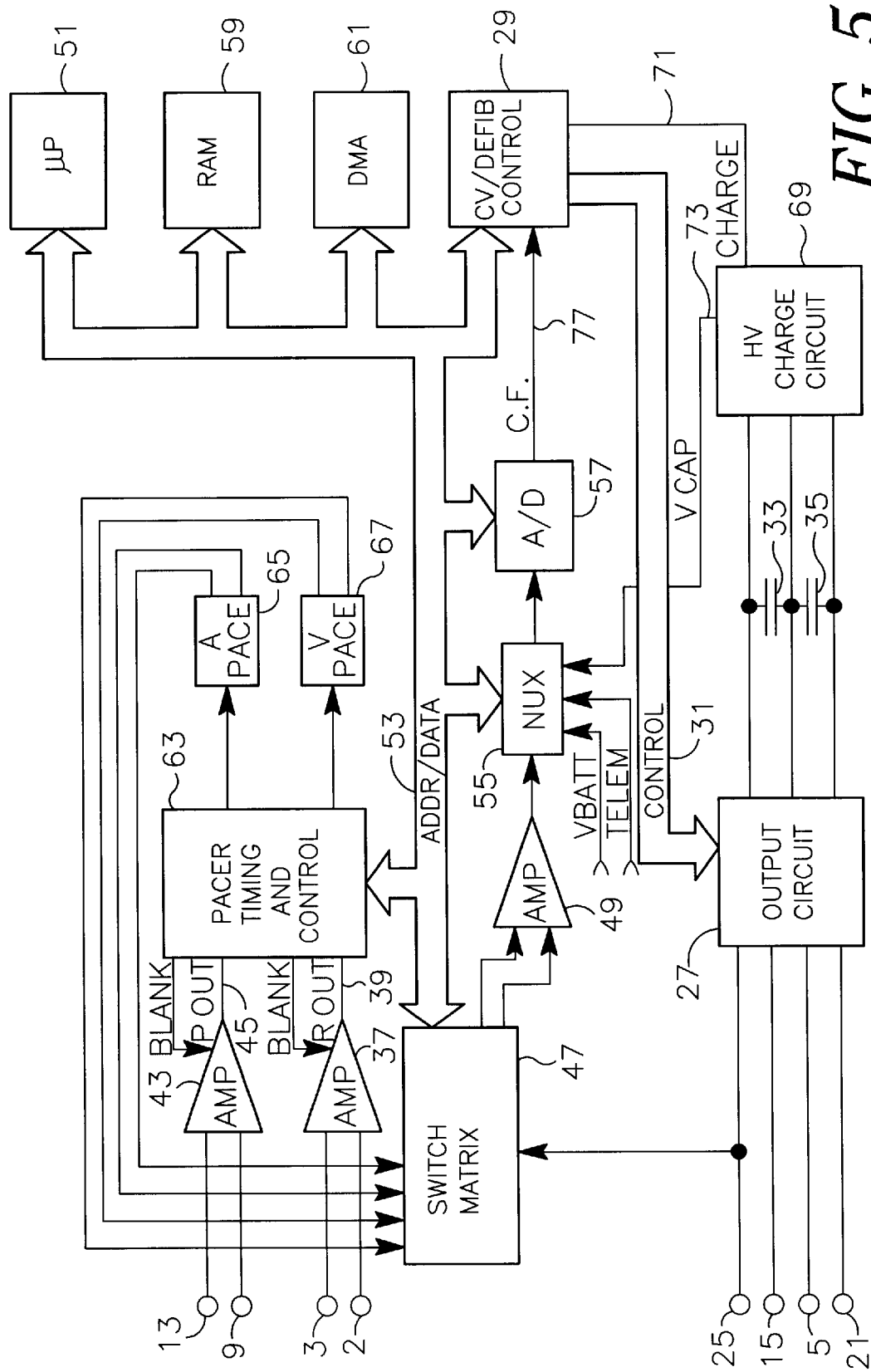
FIG. 5 is a partial block diagram illustrating one embodiment of an implantable medical device used in conjunction with the present invention.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward-facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals", hereby incorporated by reference herein in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al. and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May–June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to q cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

The entire process of the present invention has much in common with the process of diagnostic problem solving, which consists of: (1) observing findings, (2) determining possible causes of observed abnormality, and (3) suggesting tests, that, when carried out, accomplish to discriminate between the causes of the problems suspected so far. In this document, it is shown that the problem of programming/reprogramming and IMD may be viewed in such diagnostic terms.

Both IMD 10 and the excitatory and conductive system of heart 8 have a clear physical structure, which permits the use of model-based techniques. Model-based techniques are characterized by using explicit representations of structure and behavior. In particular, the theory of model-based diagnosis offers an attractive set of tools. In this document, a theory of model-based diagnosis, based on abductive diagnosis, that has been adapted to address the problems associated with IMD programming/reprogramming. Based on this theory, a system has been implemented in order to assist in programming/reprogramming an IMD. The system is incorporated into a programmer used in conjunction with an IMD. The resulting system offers a medical, model-based intelligent system that is adaptable to present day industry.

Figure 6:
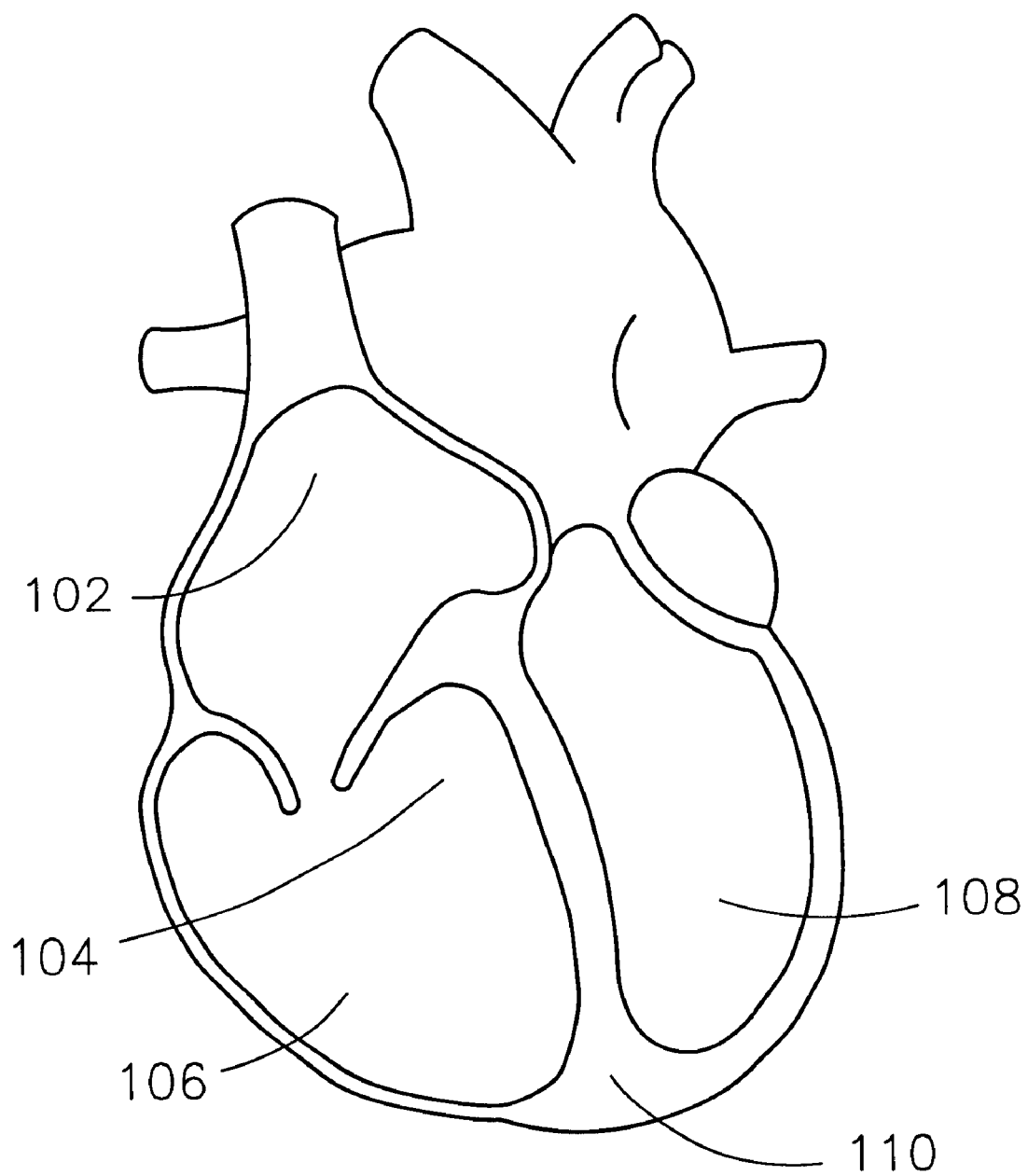
FIG. 6 is a perspective view of the excitatory and conductive system of the heart.

FIG. 6 is a perspective view of the excitatory and conductive system of the heart. Heart 8 can be viewed as a pump, responsible for maintaining blood pressure and flow within the vascular system. Continuous blood flow is required in order to deliver essential nutrients, such as oxygen and glucose, to various tissues and to remove waste products, such as carbon dioxide and urea, from the tissues to various organs for further degradation and clearance. Pressure and flow are the results of a rhythmic contraction of the cardiac muscle, the myocardium, under control of specialized excitatory and conductive cardiac tissue.

Heart 8 includes sinoatrial, or sinus, node 102, atrioventricular node 104, right ventricle 106, left ventricle 108, and conductive fibrous tissues 110. A normal human heartbeat is under the control of sinoatrial node 102, which is a small strip of specialized self-excitatory tissue, located in the wall of right atrium 106. Sinoatrial node 102 fires rhythmically at a rate in the range of approximately 50–100 beats per minute, preferably approximately 75 beats per minute. Sinoatrial node 102 generates an electrical impulse, called an action potential, which spreads through the atrial muscle wall, causing the atrial muscle to contract. The impulse travels through a muscular fiber pathway to right ventricle 106, where the impulse causes atrial ventricle node 104 to fire. The generated impulse travels quickly through the right and left bundled branches, which consist of conductive fibrous tissue 110, to the muscular tissue of right and left ventricles 106 and 108 through Purkinje fibers. Ventricular muscular tissue responds by a contraction.

There are a number of diseases which may cause the excitatory and conductive system of heart 8 to fail. This may give rise to too low of a heart rate, referred to as bradycardia, or too high of a heart rate, referred to as tachycardia. Bradycardia and tachycardia may be caused by dysfunction of sinoatrial node 102, which in turn is caused by a number of different disorders, such as disorders that cause infiltration of the myocardium with substances like amyloid. The term 'sick sinus syndrome' refers to a combination of symptoms, such as dizziness, fatigue, fainting, and heart failure, due to dysfunction of sinoatrial node 102. There are a number of other disorders of the excitatory and conductive system of heart 8, located at different parts of the overall system, that may give rise to bradycardia or tachycardia. Long-term treatment of bradycardia or tachycardia is accomplished by implantation of an IMD. As previously discussed, an IMD is capable of taking over the rhythmic contraction of the cardiac muscle, thus replacing the function of the natural IMD, i.e., sinoatrial node 102.

IMD 10 is not only capable of stimulating, or pacing, heart 8, but also capable of sensing intrinsic activity of heart 8. Sensed activity is used as information for IMD 10 to decide whether or not stimulation of heart 8 is required. IMD 10 is also capable of adapting its pacing rate depending on the needs of the patient. This capability is called rate responsiveness. An example of an advanced IMD is Vitatron's Diamond II pacemaker. IMD 10 stores and collects a variety of information, called diagnostics, which may be used in diagnosing problems associated with heart 8. Table 2 includes various information categories and the type of information associated with each category.

TABLE 2

| INFORMATION CATEGORY | TYPE OF INFORMATION |
| --- | --- |
| Patient-Specific Information | Patient's name, age, date of implantation, etc. |
| IMD Settings | Parameter values that determine the behavior of the IMD |
| Counters | Information collected based upon a frequency of occurrence of certain events |
| Histograms | Graphical information related to the distribution of certain events |
| Holters | Information relating to certain events over a particular period of time. |

There are numerous diagnostics that may be collected and stored in the categories shown in Table 2. For example, a counter entitled AV synchrony percentage expresses the percentage of cardiac events in which an atrial contraction is followed by a ventricle contraction. Another example is a P-wave histogram, which offers information on the frequency distribution of P-wave amplitudes. Finally, a 24-hour holter includes information regarding the mean heart rate, measured every specific interval, such as every six minutes, for a specified time period, such as a 24-hour period.

Cardiac symptoms and signs in a patient with an IMD can be due to a variety of problems, either medical, due to an IMD fault or failure, or both. Various problems or issues may arise with respect to an IMD. For example, Table 3 highlights various causes of atrial sensing and pacing problems. However, it is understood that Table 3 is only a subset of the types of problems that may occur associated with an IMD. Those skilled in the art understand that numerous other types of known problems may occur associated with various aspects of IMD 10, such as ventricle sensing and pacing problems and/or a combination of atrial and ventricle sensing and pacing problems.

TABLE 3

| IMD PROBLEM | SPECIFICS FOR IMD PROBLEM |
| --- | --- |
| Atrial Undersensing | Impulses generated by sinoatrial node 102 may not be sensed, thereby causing IMD 10 to generate an unnecessary impulse |
| Atrial Oversensing | IMD 10 may sense an impulse, which however, has not been generated by sinoatrial node 102 |
| Loss of Atrial Capture | IMD 10 may produce an electrical impulse, which however, fails to stimulate the atrium |

Atrial undersensing may be due to a simple problem such as atrial lead dislocation, which is a lead tip that has lost contact with the surface of the atrium. Atrial undersensing may also be due to an inner or outer insulation break, a lead conductor fracture, or a connector problem where the lead is not sufficiently attached to the connector part of IMD 10.

A typical cause of atrial oversensing is due to electromagnetic interferance by an external source. One possible cause of loss of atrial capture is an increase in the energy threshold, due, for example, to a fibrous tissue barrier to stimulation around a lead tip.

The types of problems shown in Table 3 give rise to what is called 'pacemaker syndrome.' During pacemaker syndrome, a patient may feel a beat in the neck, due to the regurgitation of ventricular blood through the atrial ventricular valve, which travels back into the atria, caused by asynchrony.

When particular problems with an IMD are suspected by a clinician or cardiologist, diagnostic tests may be carried out in order to obtain further information about possible faults or failures of components of the IMD. Some diagnostic tests can be performed directly, yielding immediate test results. Conversely, other test results are available only after some delay. It is understood by those in the art that numerous tests and types of tests may be performed in aiding a clinician in identifying faults or failures of components of the IMD. An example of a test that offers immediate results is the measurement of the atrial lead impedance. An increase in the lead impedance may be caused by a variety of factors, such as an atrial lead conductor fracture. A decrease in the lead impedance may be due to an insulation break. A test that takes more time, yielding results that are usually available only after a time delay, is for example, the ventricular output test. During this test, the cardiac output is raised to find out whether there is atrial-ventricular cross-talk.

When there are particular symptoms or signs associated with the IMD or the patient, indicating sub-optimal IMD settings, IMD faults, or medical disorder, the possible causes should be determined and action should be taken to correct the symptoms. The theory of model-based diagnosis offers several ways in which such a diagnostic process can be described. Conceptually, the diagnostic process of the present invention may be described in terms of matching abnormal behavior (MAB) diagnosis, as schematically shown in FIG. 7.

Figure 7:
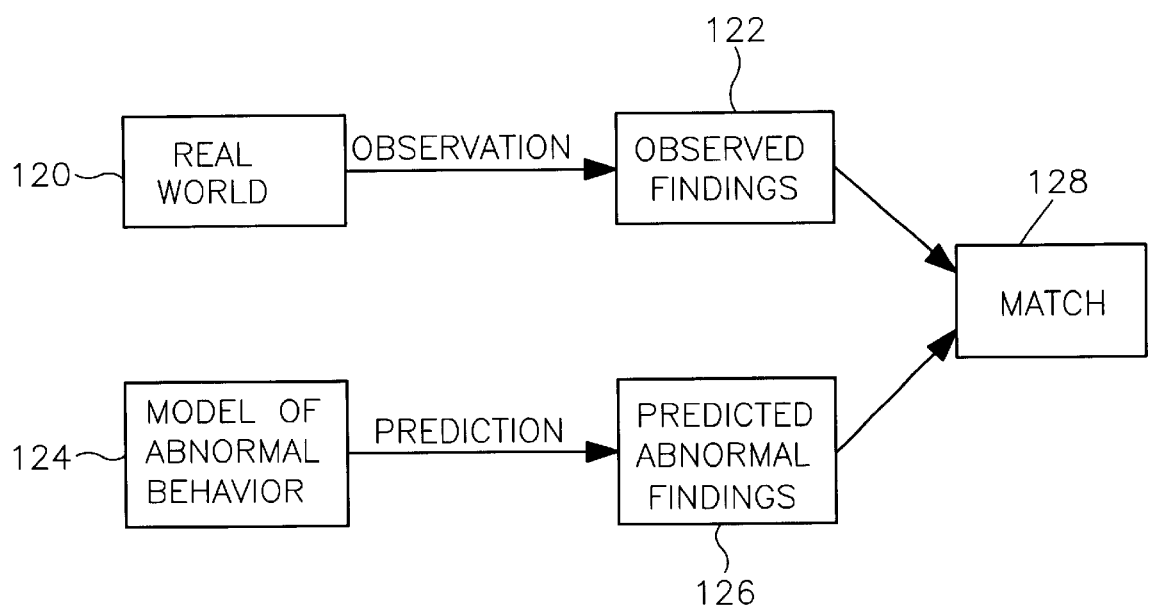
FIG. 7 is a schematic representation of matching abnormal behavior diagnosis.

FIG. 7 includes real world 120, observed findings 122, model of abnormal behavior (conditions) 124, predicted abnormal findings 126, and match 128. In MAB diagnosis, model of abnormal behavior (conditions) 124 is used to predict predicted abnormal findings 126 that must be observed. Predicted abnormal findings 126 are then matched with observed findings 122 in order to produce match 128. A collection of causes described in the model and associated with predictions that best match the findings observed are formulated into a diagnosis. Since MAB diagnosis is a conceptual model, it is typically formalized in terms of abductive reasoning or abductive diagnosis.

In the abductive diagnosis theory of the present invention, abnormal behavior or conditions of a system is represented as causal knowledge, resulting in both abnormal states and abnormal findings. Abnormal states can further be defined as defects, which may be a variety of causes or situations, varying from, for example, disorders in a patient, incorrect IMD settings, or IMD faults.

It is assumed that causal knowledge can be represented in Horn formula of the following two forms:

$$d_1 \wedge \ldots \wedge dn \rightarrow f \qquad 1.)$$

$$d_1 \wedge \ldots \wedge dn \rightarrow d \qquad 2.)$$

where $d_1$–$d_n$ represent defects and f represents an observable finding, such that a combination of defects leads to an observable finding (Equation 1) or leads to a defect (Equation 2).

A simple mechanism is proposed to weaken the above-described causality relationship, by means of literal i. The literals represent incompleteness of knowledge with respect to the underlying causal mechanisms relating cause and effects. The literal can be used to block the deduction of a finding f or defect d if the defects hold true, but the literal i is assumed to be false. The weakened Horn formula has the following form:

$$d_1 \wedge \ldots \wedge dn \wedge i_f \rightarrow f \qquad 3.)$$

$$d_1 \wedge \ldots \wedge dn \wedge i_d \rightarrow d \qquad 4.)$$

The literal i is called 'incompleteness-assumption literals,' abbreviated 'assumption literal.'

A causal specification C is defined by the following equation:

$$C = (X, Y, Z) \qquad 5.)$$

Where X denotes a set of possible (positive and negative) defects and assumption literals further defined by Equation 6.

$$X = X_P \cup Y_N \qquad 6.)$$

Where $X_P$ represents a set of positive defects and assumption literals and $X_N$ represents a set of negative defects and assumption literals.

Y (in Equation 5) represents the set of possible (positive and negative) finding literals further defined in Equation 7.

$$Y = Y_P \cup Y_N \qquad 7.)$$

Wherein $Y_P$ represents the set of positive finding literals and $Y_N$ represents a set of negative finding literals.

Z (in Equation 5) represents the set of Horn formulas of the form shown in Equations 1–4. Z further represents a causal model of abnormal behaviors.

Two definitions must now be proven to further our understanding of the present invention, specifically relating to abductive diagnostic reasoning strategy.

Definition 1. If C=(X, Y, Z) is a causal specification as defined above, then a hypothesis set H, which is a subset of possible defects and assumption literal X is a prediction for a set of observable findings (fact set) F, which is a subset of possible finding literals Y, if $$Z \cup H \text{ declares } F, \qquad 8.)$$

and $$Z \cup H \text{ is satisfied.} \qquad 9.)$$

Where F represents a fact set and H represents a hypothesis set.

The notion of the prediction described in Definition 1 formalizes a prediction error shown in FIG. 7, and the resulting prediction of observable findings F corresponds to predicted abnormal findings 126 of FIG. 7.

An abductive diagnostic problem D is now defined as a pair D=(C, E,), where observed findings E is a subset of Y, called a set of observed findings if E is consistent, and C=(X, Y, Z) as defined above. The set of observed findings E corresponds to observed findings 122 of FIG. 7.

Formally, a solution to abductive diagnostic problem D can be defined in Definition 2.

Definition 2. Let D=(C, E) be an abductive diagnostic problem, where causal specification C=(X, Y, Z) and observed findings E is a subset of finding literals Y. A set of defect and assumption literals H, which is a subset of defect and assumption literals X is a solution to D, if $$Z \cup H \text{ declares } E \text{ (covering condition)} \qquad 10.)$$

$$Z \cup H \cup C \text{ does not declare } \bot \text{ (consistency condition)} \qquad 11.)$$

Where observed findings E is a subset of observable findings and system $\bot$ is a system that does not lead to an inconsistency or a state that does not exist. Set of defect and assumption literals H is minimal with respect to set inclusion, and C, further called the constraint set, is a set of formulas in first-order logic, consisting of defect and finding literals only, as previously defined in Equation 5.

There are many possible ways for defining constraint set C. One such way is Equation 12, where it is assumed that $C_1 = C$.

$$C_1 = \neg f \in Y / f \in Y, f \notin E, f \text{ is a positive literal} \qquad 12.)$$

In other words, the constraint set stands for findings assumed to be false, because they have not been observed (and are therefore assumed to be absent). This is an application of a closed world assumption, restricted to observable findings.

The covering conditions of Definitions 1 and 2 above, specifically Horn formulas Z in unity with assumption literals H declares observed findings E, ensures that sufficient defect and assumption literals are assumed to account for all given observed findings. The consistency condition of Definitions 1 and 2 (more specifically, Horn formulas Z in unity with assumption literals H is satisfiable in Definition 1, and Horn formulas Z in unity with assumption literals H in unity with causal specification C does not declare a system that leads to an inconsistency or a state that doesn't exist in Definition 2) ensures that not too many defect and assumption literals are assumed. It is only necessary to include an assumption literal i in a solution for implications D and $i_f$ leads to f and D and $i_d'$ leads to d'. If the defect d is deductible from the assumed initial defects and assumption literals, the condition of minimality with respect to set inclusions of a diagnosis implies that no more defect and assumption literals will be assumed as part of the diagnosis other than those defects and assumption literals required to predict observed findings.

In the consistency conditions as defined above, it is assumed that all findings associated with a defect, present in the real world, will be observed. If a finding is not included among the findings in the set of observed findings, it is assumed to be absent. The basic assumption is that all findings of defects which are not observed are absent. Thus, it is assumed that all findings not observed are negative. The assumption of negative literals has the technical advantage of blocking the inclusion of defects that are not present in the real world according to the theory, because some observable findings associated with the defect is not included in the set of observed findings.

However, it is not always justified to assume negative findings in this way. Sometimes, it is more natural to take the findings as being unknown. Hence, the definition of the constraint set $C_1$ discussed above may be too strong for practical purposes. When predict logic is used and particular predictions associated with findings are used as tests, the definition of $C_1$ above may be replaced by the following definition.

$$C_2 = \{\neg P(t) \in Y_N / P(s) \in E, t \neq s, \text{ or } \neg P(t) \text{ has been observed}\} \quad 13.)$$

Where P stands for predictive symbols, and t and s are constants. The consistency condition of Definition 2 (Equation 11) remains the same, but its effect on the computation of a diagnosis differs, because of the altered definition of the constraint set C. For example, if tests p, q, and r are performed, then the constraint set $C_1$ defined in Equation 12 consists of all negative finding literals p(t), q(t'), r(t'') that have not been observed, even if particular tests have not been performed. Conversely, with the definition of constraints $C_2$ of Equation 13, only negative literals concerning tests done are included and supplemented with findings explicitly observed to be absent.

In abductive diagnosis, the consistency condition $C_2$ defined in Equation 13 is similar to the consistency condition $C_1$ defined in Equation 12, except that it is assumed that if no information concerning a specific diagnostic test is available, it is assumed to be unknown. Therefore, if a defect d is included in a hypothesis H and Horn formulas Z in unity with defect d declares a fact or an observable finding f, where the fact or observable finding f is not an element of a subset of observable findings E; and if the test is actually carried out, the fact or observable finding f will be observed. This is a basis for diagnostic problem solving which suggests or prompts a clinician to carry out a particular test or tests.

In the domain of IMD programming/reprogramming, it is known that particular combinations of defects cannot occur. These impossible combinations can be represented as a set of additional domain constraints D, imposing a further limitation on the number of possible solutions. Therefore, the final definition of the constraint set used in Definition 2 is as follows:

$$C = C_2 \cup D \quad 14.)$$

The above description suggests a dynamic, diagnostic process where preliminary diagnosises and the proposal of additional tests are generated by a system. In addition, when new test information becomes available, the old diagnosis may be revised. Using the definition of abductive diagnosis given above, and the definition of a constraint set defined as consisting of absent findings, either observed or inferred, a test selection can be added to an abductive reasoning scheme. For example, let D=(C, E) be an abductive diagnostic problem, with E being the set of observed findings and C=(X, Y, Z) be a causal specification. Then, if H is a solution to D, then it may hold true that Z in unity with H declares F where F is a subset of E.

Since the solution H predicts findings that have not, as yet, been observed, and since all findings resulting from tests are included, either positively in E or negatively in C, the observable findings in the difference set F\E pertain to tests that have not yet been carried out. In this way, the abductive reasoning scheme may suggest to a clinician to perform particular diagnostic tests which have not been performed.

If a particular diagnostic test is performed, the test results may either exactly correspond to the finding previously predicted by a diagnostic solution or may turn out to be different from a previously predicted diagnostic solution. The following Lemma statement corresponds to a situation in which a test result corresponds exactly to the finding previously predicted by a diagnostic solution.

Lemma 1. Let A=(C, E) be an abductive diagnostic problem with causal specification C=(X, Y, Z), and let A'=(C, E') be an abductive diagnostic problem, such that $E' = E \cup (t_i)$. Furthermore, let the constraint set of D' be equal to C', as defined in Equation 15.

$$C' = C \cup \{\neg P(t_1)_1 \neg P(t_{i-1})_1 \neg P(t_{i+1}) \ldots \neg P(t_n)\} \quad 15.)$$

Wherein C is the constraint set of A. Finally, let H be a solution to D, such that $Z \cup H$ declares that $P(t_i)$. Then, H is also a solution to D' if:

$$Z \cup H \cup C' \text{ does not declare } \perp \quad 16.)$$

The proof of Lemma 1 is a straightforward check against Definition 2, previously discussed. Lemma 1 suggests that it is sufficient to check the satisfiability of the consistency condition as soon as information corresponding to a suggested diagnostic test result becomes available.

Lemma 2 concerns a situation where the actual observed finding is different from the finding previously predicted by a diagnostic solution.

Lemma 2. Let D=(C, E) be an abductive diagnostic solution with causal specification C=(X, Y, Z), and let D'=(C, E') be an abductive diagnostic problem, such that $E' = E \cup P(t_j)$ and C' is defined in Equation 17.

$$C' = C \cup \{\neg P(t_1) \ldots, \neg P(t_i) \ldots, \neg P(t_{j-1}), \neg P(t_{j+1}) \ldots \neg P(t_n)\} \quad 17.)$$

Where C and C' are the constraining sets of D and D', respectively. Furthermore, let H be a solution to D, such that Z in unity with H declares $P(t_i)$, where i does not equal j. Then, for any solution H', it holds that H' cannot be a subset of H and H cannot be a subset of H'.

The proof of Lemma 2 is as follows. According to the premise, it must hold true that Z in unity with H' declares P $(t_j)$ with j not equal to i, and that Z in unity with H' declares E, whereas Z in unity with H declares P $(t_i)$ and Z in unity with H declares E. From this and the montonicity of the entailment relation (declares that), it follows that H' cannot be a subset of H, otherwise Z in unity with H' in unity with C declares $\perp$. However, since Z in unity with H declares E, with H minimal with respect to set inclusion, H' cannot be a subset of H either.

Lemma 3 (below) implies that a solution computed by taking a test result into account will either be identical to an old solution or be a super set of an old solution.

Lemma 3. Let D=(C, E) be an abductive diagnostic problem with causal specification C=(X, Y, Z), and let D'=(C, E') be an abductive diagnostic problem, such that E'=E∪P(t$_i$). Furthermore, let C be the constraint set of D and C' be the constraint set of D', where C' is defined in Equation 18.

$$C' = C \cup \{\neg P(t_i), \neg P(t_{i-1}), \neg P(t_{i+1}) \ldots \neg P(t_n)\} \quad (18.)$$

If H is a solution to D', then H is also a solution to D, if for each H' (a super set of H), it holds true that Z in unity with H' does not declare E.

The proof of Lemma 3 is as follows. If Z in unity with H declares E in unity with P(t$_i$), then Z in unity with H declares E. Furthermore, if Z in unity with H in unity with C' does not declare ⊥, then Z in unity with H in unity with C does not declare ⊥. However, the set of defect and assumption literals H need not be minimal with respect to set inclusion. Hence, H may not be a solution to D, although the covering consistency conditions are fulfilled. This explains the inclusions of the extra condition in the premise.

Up to this point, the order of performing diagnostic tests as suggested by the system to a clinician has not been discussed. However, in programming/reprogramming an IMD, consecutive steps of the diagnostic cycle should be followed. In particular, a structured fashion of gaining information based upon previously gathered information will aide in a proper programming/reprogramming procedure and optimize the time of programming/reprogramming.

Diagnostic solutions that are causally related to findings that have not yet been observed may give rise to requests for further information. Since new information may affect the validity of previous solutions, these solutions are categorized into three distinct categories: suspected solutions, rejected solutions, and confirmed solutions. Suspected solutions predict at least one finding that may be obtained by a test that has not yet been carried out. Rejected solutions are solutions to a previous problem, which are now rejected because of the availability of new, additional evidence, that somehow refutes the previous solution. Confirmed solutions are solutions in which all predicted, associated tests have been carried out, and the observed results appear to correspond to the results predicted. Incorporating such a distinction between various solutions in a diagnostic reasoning method is part of a diagnostic strategy. The overall structure of this diagnostic strategy, as applied to programming/reprogramming an IMD, is depicted in FIG. 8.

Figure 8:
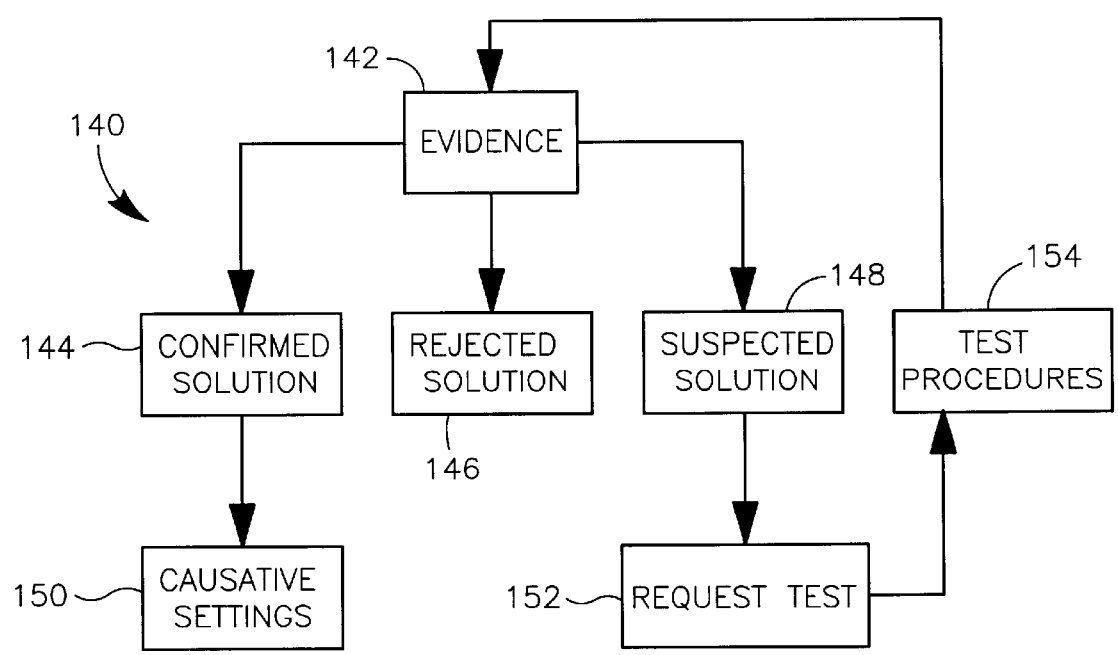
FIG. 8 is a flow chart illustrating a problem solving strategy in accordance with the present invention.

FIG. 8 is a flow chart illustrating problem solving strategy 140 of the present invention. Problem solving strategy 140 includes evidence 142, confirmed solutions 144, rejected solutions 146, suspected solutions 148, causative settings 150, requested tests 152, and test procedure 154. As shown in FIG. 8, problem solving strategy 140 begins with gathering evidence 142. Evidence 142 may be gathered by various means, such as by a clinician conversing directly with the patient or observing or examining the patient. The evidence may also be gained via a programmer in communication with an IMD. In addition, evidence may be gathered through other means, such as by a clinician reviewing various manuals or text.

Each piece of evidence 142 may be categorized into either confirmed solutions 144, rejected solutions 146, or suspected solutions 148 as previously discussed. If evidence 142 is categorized into confirmed solutions 144, causative settings 150 may be provided to the clinician, suggesting to the clinician the optimal setting for the associated IMD. Causative settings 150 may be provided to the clinician in a variety of means, such as audio or visual means. In a one embodiment, display screen 206 of programmer 200 shown in FIG. 11 may be used as a conduit for providing causative settings 150 to the clinician.

If evidence 142 is categorized into projected solutions 146, solutions to a previous problem are now rejected because of the availability of new evidence (evidence 142) which refutes a previous solution. Finally, if evidence 142 is categorized into suspected solutions 148, it is predicted that at least one finding that may be obtained by a test that has not yet been carried out may be confirmed or rejected. Therefore, requested test 152 initiates test procedure 154 in which new evidence (evidence 142) may be determined.

Strategic control of diagnostic reasoning not only concerns the process of hypothesis generating and testing, but the process of gathering relevant evidence as well. In diagnostic probabilistic systems, the gathering of evidence is frequently guided by taking the expected contribution of the evidence into account. A popular measure of the expected contribution of evidence is the notion of "value of information." Such a measure is not available for qualitative systems. However, as stated above, in many domains information is collected in a structured fashion, and this structure can also be used as a basis for evidence gathering.

In the case of programming/reprogramming an IMD, the gathering of evidence may be structured in such a way that IMD settings and diagnostics, which are readily available from an IMD, are always requested first. Next, information from follow-up procedures, i.e., information that requires some extra tests, yielding results that are also immediately available, are requested. Finally, information obtained after a period of time from additional tests, such as a chest radiograph, can be taken as a last source of evidence.

Figure 9:
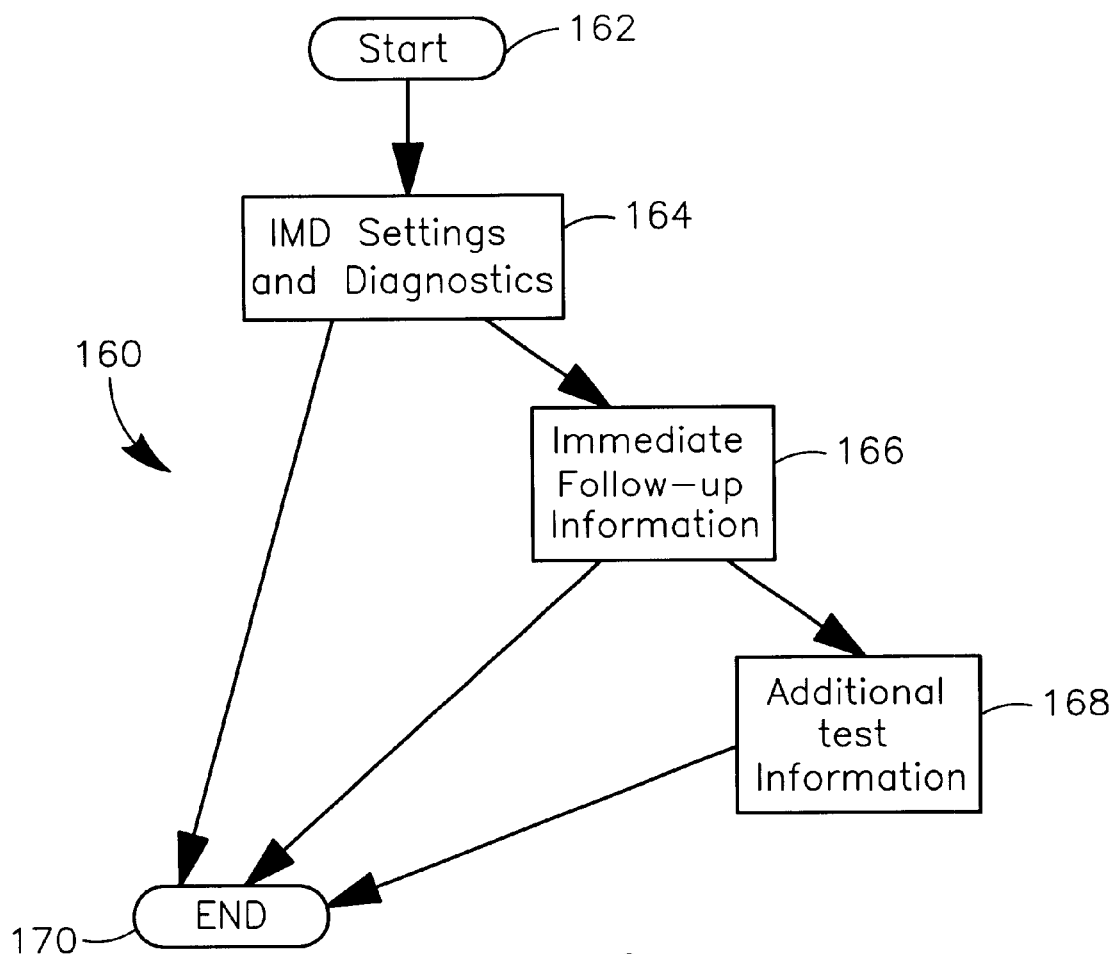
FIG. 9 is a flow chart illustrating one structure for information gathering in accordance with the present invention.

FIG. 9 is a flow chart illustrating one structure for information gathering in accordance with the present invention. As shown in FIG. 9, flow chart 160 includes start 162. From start 162, IMD settings and diagnostics 164 are gathered, which are readily available from an IMD. If enough information is gathered from IMD settings and diagnostics 164 to provide optimal IMD therapy, the information gathering is completed at end 170. However, if additional evidence is to be gathered, information may be obtained at immediate follow-up information 166, which requires gathering immediate information and yields results that are immediately available. At this point, if enough information has been gathered to provide optimal IMD therapy, the gathering process ends at step 170. However, if yet additional information is necessary, information can be obtained from additional tests as shown at additional test information 168. The tests performed within additional test information 168 of those tests which require a period of time prior to obtaining the results.

It is possible to order resulting multiple solutions by taking the number of assumption literals, as previously defined, occurring in each individual solution into account. This number may be taken as a simple, qualitative measure of uncertainty of a given solution. Obviously, solutions with no assumption literals included will be more likely than those with one more assumption literals included. Since it is undesirable to neglect even unlikely solutions, this approach to the ordering of diagnostic solutions may be adequate in the IMD domain. Furthermore, solutions with an equal number of assumption literals can be ordered according to the number of defect literal elements, indicating that solutions that include many defect literals are less likely than those with fewer defect literals.

Figure 10:
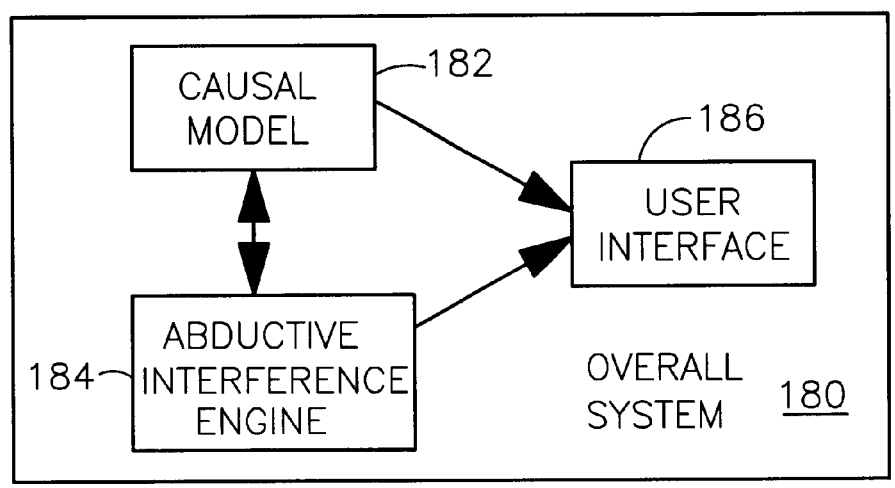
FIG. 10 is a block diagram illustrating the overall system of the present invention.

As shown in FIG. 10, overall system 180 of the present invention is divided into three specific elements; causal model 182, abductive inference engine 184, and user interface 186. It is understood by those in the art that overall system 180 and its components may be located solely within a programmer used in conjunction with an IMD, such as programmer 200 shown in FIG. 11. Conversely it is understood that portions of overall system 180 may reside in a programmer, while other portions may reside in an IMD, such that overall system 180 includes both elements.

Abductive inference engine 184 of overall system 180 has previously been described with reference to the abductive diagnostic theory and causal knowledge, particularly the discussion associated with Equations 1–19, Definitions 1 and 2, and Lemmas 1, 2, and 3. In particular, Definition 2 and Lemma 3 provide the abductive inference engine for overall system 180. It is understood by those in the art that abductive inference engine 184 may be implemented in various ways, one of which is by incorporating abductive inference engine 184 into a software program installed in conjunction with a microprocessor in either an IMD or a programmer, such as programmer 200, shown in FIG. 11.

User interface 186 is further described with reference to FIG. 11. FIG. 11 is a perspective view of programmer unit 200, which, in one embodiment, corresponds to user interface 186. It is understood by those in the art that other programmers known in the art may be substituted for programmer 200 without deviating from the present invention. Programmer 200 is a microprocessor based device which includes various features, such as outer housing 202, carrying handle 204, articulate display screen 206, stylus 208, and analyzer 210.

Display screen 206 is disposed on the upper surface of housing 202. Display screen 206 folds down in a close position when programmer 200 is not in use, thereby reducing the size of programmer 200 and protecting the display surface of display screen 206 during transportation and storage. Display screen 206 is operatively coupled to computer circuitry disposed within housing 202 and is adapted to provide a visual display of graphics and/or numerical and alphanumeric data under control of the computer circuitry.

Display screen 206 is provided with touch-sensitivity capability, such that a user can interact with the internal computer by touching the display area of display screen 206 with stylus 208. It is believed that those of ordinary skill in the computer art will be familiar with touch-sensitivity display technology, and the details of implementation of such display will not be described further herein. Display screen 206 is the primary input medium for programmer 200 and therefore preferably has sufficient resolution to support operations including selection, gestures, annotation, and character recognition.

Analyzer 210, which can be a separate unit capable of connection to programmer 200 via connecting cables, is a microprocessor based device which provides a medium for an operator to run a series of diagnostic tests during an implantation procedure of an IMD, such as IMD 10 previous discussed. For example, a continuous-time wave form or single complex wave form can be analyzed by analyzer 210 and displayed on display screen 206 from a variety of implanted leads, such as a lead position in an atrium or ventricle of heart 8 (shown in FIGS. 1, 2, and 4).

Figure 12:
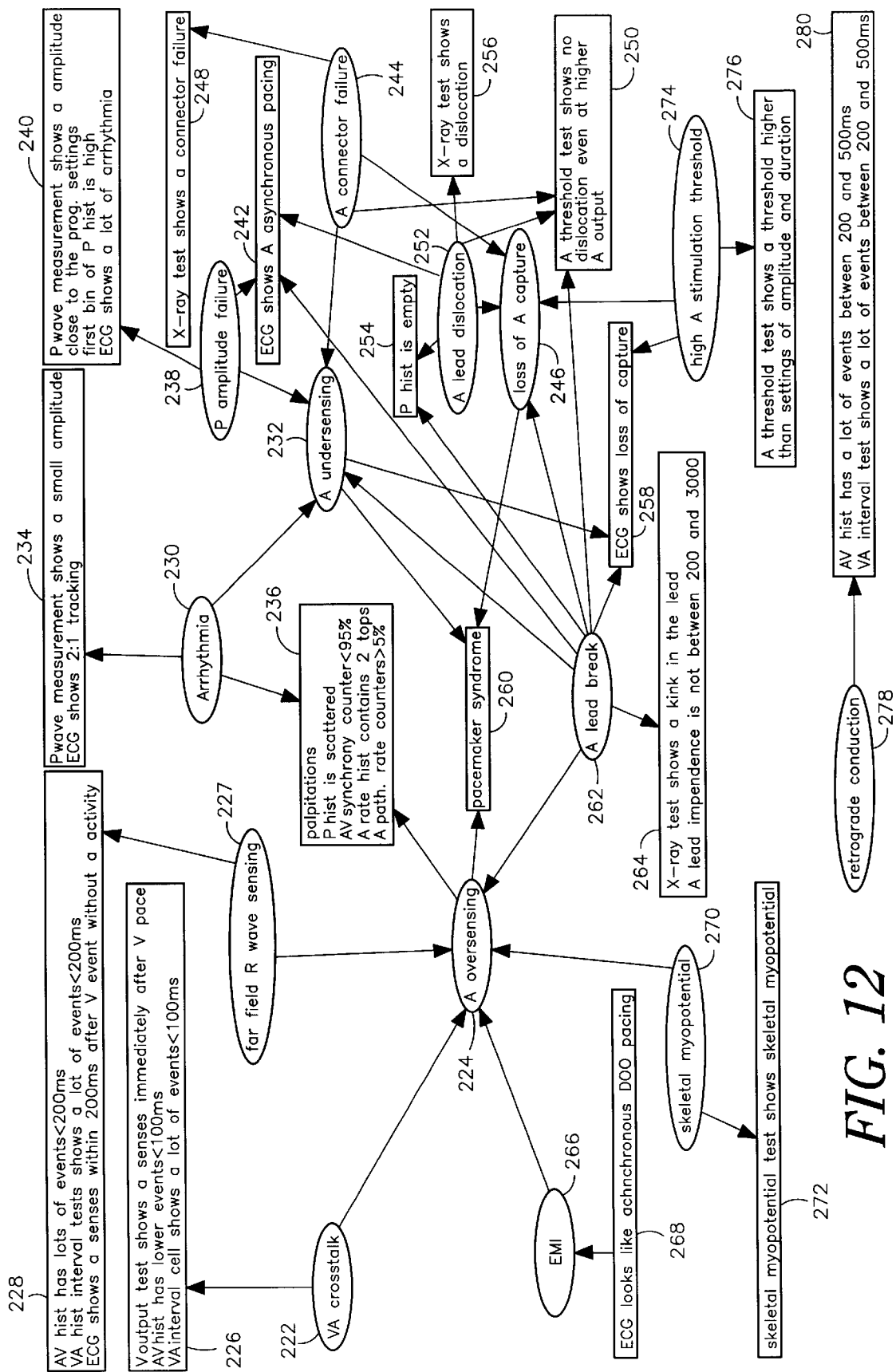
FIG. 12 is a flow chart illustrating a portion of a causal model of abnormal implantable medical device behavior.

Flow chart 220, shown in FIG. 12, is a causal model of abnormal atrial behavior. Thus, flow chart 220 represents a specific portion of causal model 182 shown in FIG. 10. It is understood by those in the art that abnormal atrial behavior is merely a subset of all abnormal behavior relating to a patient or an IMD. Therefore, it is understood that abnormal behavior relating to the ventricle or other portions of the heart, or to an IMD in particular, may be present. However, for clarity purposes of the present case, these abnormalities will not be further described. It is further understood by those in the art that causal model 182, similar to abductive diagnostic engine 184, may be implemented in various ways, one of which is by incorporating causal model 182 into a software program installed in conjunction with a microprocessor in either an IMD or a programmer, such as programmer 200, shown in FIG. 11.

Ellipses in flow chart 220 represent "defects" while rectangular vertices represent "tests and associated test results". The direction of each arrow in flow chart 220 mirrors a cause-effect relationship. The interaction between various defects associated with a single test and associated test result are disjunctive. Each of the causes is considered sufficient for producing the effect. Within flow chart 220, no explicit distinction between weakly and strongly causal relationships is indicated.

Ellipse 222 represents ventricle atrial cross-talk. This defect may take place if atrial blanking occurs at less than 50 milliseconds or if atrial sensitivity occurs at less than 0.5 millivolts. Ventricle atrial cross-talk 222 may result in atrial oversensing as indicated by ellipse 224. If ventricle atrial cross-talk occurs, various tests can be performed, as shown in rectangle 226. For example, a ventricle output test may be performed showing an atrial sense immediately after a ventricle pace. An atrial ventricle histogram may indicate several events under 100 milliseconds. Further, a ventricle atrial interval test may show multiple events under 100 milliseconds.

Far field R-wave sensing, as illustrated by ellipse 227 may result in atrial oversensing 224 or may result in various tests as shown in rectangle 228. As shown in rectangle 228, an atrial ventricle histogram may indicate a series of events under 200 milliseconds. Also, a ventricle atrial histogram interval test may show several events under 200 milliseconds. In addition, an electrocardiogram may show an atrial sense within 200 milliseconds after a ventricle event without a corresponding atrial activity.

Arrhythmia, as represented by ellipse 230, may cause atrial undersensing, as shown in ellipse 232, or may result in various tests to be performed. For example, rectangle 234 includes a P-wave measurement which shows a small amplitude or an electrocardiograph which shows a 2:1 tracking ratio. Further, as shown in rectangle 236, may be performed. For example, palpitations may be identified, or a P-wave histogram may be scattered, or an atrial ventricle synchrony counter may be less than 95 percent, or an atrial rate histogram may contain two tops, or atrial rate counters may be greater than 5 percent.

A P-wave amplitude failure, as shown in ellipse 238 may result in atrial undersensing, as shown in ellipse 232, or may result in a P-wave measurement which shows an amplitude close to the program settings, or may indicate a first bin of a P-wave histogram is high, or an electrocardiogram may show numerous arrhythmia, as shown in rectangle 240. Also, as shown in box 242, electrocardiogram may show an atrial asynchronous pacing.

A connector failure, as represented by ellipse 244, may result in atrial undersensing, as shown in ellipse 232, a loss of atrial capture as shown at ellipse 246. Connector failure 244 may also result in an X-ray test showing a connector failure, as shown at rectangle 248, or a threshold test may show no caption even at highest atrial output, as shown at rectangle 250.

Atrial lead dislocation, as shown in ellipse 252, may result in a P-wave histogram being empty, as shown at rectangle 254 an X-ray test showing a dislocation, as shown at rectangle 256, an electrocardiogram showing a loss of capture, as illustrated at rectangle 258, atrial undersensing, as shown at ellipse 232, a loss of atrial capture, as shown at ellipse 246, or an electrocardiogram may show atrial asynchronous pacing, as shown at rectangle 242.

Atrial oversensing 224 may result in all of the tests and test results shown in rectangle 236 and previous discussed, or may result in the pacemaker syndrome, as shown in rectangle 260. Similarly, loss of atrial capture, as shown in ellipse 246 may result in the pacemaker syndrome as shown at rectangle 260.

Atrial lead break 262 may result in atrial oversensing or atrial undersensing as shown at ellipses 224 and 232, respectively. In addition, an atrial lead break may also indicate a loss of atrial capture as shown at ellipse 246. Further, as shown in rectangle 254, a P-wave histogram may be empty, or a threshold test may show no capture even at high atrial outputs, as shown in rectangle 250, or an electrocardiogram may show loss of capture, as shown at rectangle 258. Furthermore, an atrial lead break may result in an X-ray test showing a kink in the lead, or an atrial lead impedance which is not between 200 and 3,000 ohms, as shown in rectangle 264 or an electrocardiogram may show an atrial asynchronous pacing, as shown in rectangle 242.

EMI, as shown at ellipse 266 may result in atrial oversensing, as shown in ellipse 224, or may result in an electrocardiogram which looks asynchronous DOO pacing, as shown at rectangle 268. Skeletal myopotential, as shown at ellipse 270, may result in atrial oversensing or may result in skeletal myopotential tests which show skeletal myopotential, as shown at rectangle 272.

High atrial stimulation threshold, as shown at ellipse 274, may result in a loss of atrial capture, or may result in an electrocardiogram showing loss of capture, as shown in ellipse 246, or may result in a threshold test showing a threshold higher settings of amplitude and duration, as shown at rectangle 276.

A retrograde conduction, as shown at ellipse 278 may result in various tests, shown at rectangle 280, such as an atrial ventricle histogram having various events between 200 and 500 milliseconds, or a ventricle atrial interval test showing various events between 200 and 500 milliseconds.

Abductive inference engine 184 interacts with causal model 182 in order to determine one or more revisions or reprogramming steps for an IMD. The revisions or reprogramming steps are then provided to a clinician via user interface 186, which in one embodiment is programmer 200. It is understood by those in the art that all components of overall system 180 are capable of interfacing with all other components, if necessary.

Overall system 180 has been evaluated utilizing 19 patients having sensing or pacing problems of the atrium. Only one of the 19 patients had symptoms caused by a combination of problems (far field R-wave sensing combined with a too low P-wave amplitude). Results in which the conclusions of an expert clinician were checked against the conclusions of overall system 180 are shown in FIG. 13. Note that only incorrect advice was concerning the single patient who had a combined problem. Actually, in this particular case, system 180 diagnosed that there was a far field R-wave sensing problem, but did not reach the inclusion that the P-wave amplitude was too low in this patient.

The results obtained by comparing the diagnosis generated by overall system 180 with the conclusions of a clinician expert are summarized in FIG. 14. The single case were only one of two problems was diagnosed is classified as being incorrect.

The proceeding specific embodiments are illustrative of the practice of the invention. It is understood to be, therefore, that other expedients known to those skilled in the art or disclosed herein, may be employed without departing from the invention or the scope of the appended claims. For example, the present invention is not limited to abductive diagnostic reasoning with respect to any particular subsection of an overall IMD system, such as the atrial or ventricle portion of an IMD system. Rather, the invention may be used for diagnosis of any particular subset of an overall IMD system, or may be used for diagnosis of the entire system.

The present invention is also not limited to pacemakers or defibrillators per se, but may find further applications with other IMDs which are capable of being programmed/reprogrammed. The present invention further includes within its scope methods of making and using the implantable medical device described herein.

In the claims section of this application, means-plus-function clauses are intended to cover the structures described herein as performing the recited function and not only structural equivalents but also equivalent structures. For example, although a nail and a screw may not be structurally equivalent in that a nail employs a cylindrical surface to secure wooden parts together, whereas a screw employs a helical surface, in the environment of fastening wood parts, a nail and a screw are equivalent structures.

Although specific embodiments of the invention have been set forth herein in some detail, it is understood that this has been done for the purposes of illustration only and is not to be taken as a limitation on the scope of the invention as defined in the appended claims. It is to be understood that various alterations, substitutions, and modifications may be made to the embodiment described herein without departing from the spirit and scope of the appended claims.

What is claimed is:

1. An implantable medical device system capable of providing diagnostic information to a clinician relating to optimal settings for a specific patient, the system comprising:

a causal model coupled to an implantable medical device and capable of identifying at least one cause of an abnormal condition;

an abductive inference engine coupled to the causal model and capable of identifying a suggested updated setting for the implantable medical device to alleviate the abnormal condition; and a display coupled to the causal model for displaying the abnormal behavior and the suggested updated settings.

2. The implantable medical device system of claim 1, and further comprising:

a microprocessor coupled to the causal model and capable of identifying at least one abnormal condition.

3. The implantable medical device system of claim 2, wherein the microprocessor is capable of identifying at least one abnormal implantable medical device setting condition.

4. The implantable medical device system of claim 2, wherein the microprocessor is capable of identifying at least one abnormal counter condition.

5. The implantable medical device system of claim 2, wherein the microprocessor is capable of identifying at least one abnormal histogram condition.

6. The implantable medical device system of claim 2, wherein the microprocessor is capable of identifying at least one abnormal holter condition.

7. The implantable medical device system of claim 1, wherein the causal model is capable of identifying at least one abnormal condition relating to the implantable medical device.

8. The implantable medical device system of claim 1, wherein the causal model is capable of identifying at least one abnormal condition relating to the patient.

9. The implantable medical device system of claim 1, wherein the causal model is capable of identifying at least one abnormal condition relating to an atrial event.

10. The implantable medical device system of claim 1, wherein the causal model is capable of identifying at least one abnormal condition relating to a ventricle event.

11. The implantable medical device system of claim 1, wherein the causal model is capable of identifying at least one abnormal condition relating to a pacing event.

12. The implantable medical device system of claim 1, wherein the causal model is capable of identifying at least one abnormal condition relating to a sensing event.

13. The implantable medical device system of claim 1, wherein the abductive inference engine utilizes an abductive diagnostic reasoning strategy as a basis for identifying the suggested updated setting.

14. The implantable medical device system of claim 1, wherein the abductive inference engine evaluates at least one implantable medical device setting in identifying suggested updated setting for the implantable medical device.

15. The implantable medical device system of claim 1, wherein the abductive inference engine evaluates information based upon test procedures completed after an initial identification of an abnormal behavior.

16. The implantable medical device system of claim 1, wherein the abductive inference engine includes at least one assumption literal.

17. The implantable medical device system of claim 1, wherein the causal model is incorporated into a software program capable of being executed by an implantable medical device programmer.

18. The implantable medical device system of claim 1, wherein the abductive inference engine is incorporated into a software program capable of being executed by an implantable medical device programmer.

19. The implantable medical device system of claim 1, wherein the causal model is incorporated into a software program capable of being executed by an implantable medical device.

20. The implantable medical device system of claim 1, wherein the abductive inference engine is incorporated into a software program capable of being executed by an implantable medical device.

21. A method of providing information to a clinician relating to settings of an implantable medical device for a specific patient, the method comprising:

identifying at least one abnormal condition associated with the implantable medical device;

identifying at least one possible revised implantable medical device setting;

identifying the optimal revised implantable medical device setting; and displaying the optimal revised implantable medical device setting.

22. The method of claim 21, wherein the step of identifying at least one abnormal condition further comprises:

identifying at least one abnormal implantable medical device setting condition.

23. The method of claim 21, wherein the step of identifying at least one abnormal condition further comprises:

identifying at least one abnormal counter condition.

24. The method of claim 21, wherein the step of identifying at least one abnormal condition further comprises:

identifying at least one abnormal histogram condition.

25. The method of claim 21, wherein the step of identifying at least one abnormal condition further comprises:

identifying at least one abnormal holter condition.

26. The method of claim 21, wherein the step of identifying at least one abnormal condition further comprises:

identifying at least one abnormal condition relating to an atrial event.

27. The method of claim 21, wherein the step of identifying at least one abnormal condition further comprises:

identifying at least one abnormal condition relating to a ventricle event.

28. The method of claim 21, wherein the step of identifying at least one abnormal condition further comprises:

identifying at least one abnormal condition relating to a pacing event.

29. The method of claim 21, wherein the step of identifying at least one abnormal condition further comprises:

identifying at least one abnormal condition relating to a sensing event.

30. The method of claim 21, wherein the step of identifying the optimal revised implantable medical device setting further comprises:

utilizing an abductive diagnostic reasoning strategy.

31. The method of claim 21, wherein the step of identifying the optimal revised implantable medical device setting further comprises:

evaluating at least one implantable medical device setting.

32. The method of claim 21, wherein the step of identifying the optimal revised implantable medical device setting further comprises:

evaluating information based upon test procedures completed after the step of identifying at least one abnormal behavior associated with the implantable medical device.

33. The method of claim 21, and further comprising:

performing at least one additional diagnosis test; and identifying the optimal revised implantable medical device setting based upon the at least one possible revised implantable medical device setting in conjunction with the at least one additional diagnostic test.

34. A system for providing information to a clinician relating to optimal setting of an implantable medical device for a specific patient, the system comprising:

means for identifying at least one abnormal behavior associated with the implantable medical device;

means for identifying at least one possible revised implantable medical device setting;

means for identifying the optimal revised implantable medical device setting; and means for displaying the optimal revised implantable medical device setting.

35. The system of claim 34, wherein the means for identifying at least one abnormal condition further comprises:

means for identifying at least one abnormal implantable medical device setting condition.

36. The system of claim 34, wherein the means for identifying at least one abnormal condition further comprises:

means for identifying at least one abnormal counter condition.

37. The system of claim 34, wherein the means for identifying at least one abnormal condition further comprises:

means for identifying at least one abnormal histogram condition.

38. The system of claim 34, wherein the means for identifying at least one abnormal condition further comprises:

means for identifying at least one abnormal holter condition.

39. The system of claim 34, wherein the means for identifying at least one abnormal condition further comprises:

means for identifying at least one abnormal condition relating to the implantable medical device.

40. The system of claim 34, wherein the means for identifying at least one abnormal condition further comprises:

means for identifying at least one abnormal condition relating to the patient.

41. The system of claim 34, wherein the means for identifying at least one abnormal condition further comprises:

means for identifying at least one abnormal condition relating to an atrial event.

42. The system of claim 34, wherein the means for identifying at least one abnormal condition further comprises:

means for identifying at least one abnormal condition relating to a ventricle event.

43. The system of claim 34, wherein the means for identifying at least one abnormal condition further comprises:

means for identifying at least one abnormal condition relating to a pacing event.

44. The system of claim 34, wherein the means for identifying at least one abnormal condition further comprises:

means for identifying at least one abnormal condition relating to a sensing event.

45. The system of claim 34, wherein the means for identifying the optimal revised implantable medical device setting further comprises:

means for utilizing an abductive diagnostic reasoning strategy.

46. The system of claim 34, wherein the means for identifying the optimal revised implantable medical device setting further comprises:

means for evaluating at least one implantable medical device setting.

47. The system of claim 34, wherein the means for identifying the optimal revised implantable medical device setting further comprises:

means for evaluating information based upon test procedures completed after the step of identifying at least one abnormal behavior associated with the implantable medical device.

48. The system of claim 34, and further comprising:

means for performing at least one additional diagnosis test; and means for identifying the optimal revised implantable medical device setting based upon the at least one possible revised implantable medical device setting in conjunction with the at least one additional diagnostic test.

49. A method of providing information to a clinician relating to optimal settings of an implantable medical device for a specific patient, the method comprising:

identifying at least one abnormal condition associated with the patient;

identifying at least one possible revised implantable medical device setting;

identifying the optimal revised implantable medical device setting; and displaying the optimal revised implantable medical device setting.

50. The method of claim 49, wherein the step of identifying at least one abnormal condition further comprises:

identifying at least one abnormal counter condition.

51. The method of claim 49, wherein the step of identifying at least one abnormal condition further comprises:

identifying at least one abnormal histogram condition.

52. The method of claim 49, wherein the step of identifying at least one abnormal condition further comprises:

identifying at least one abnormal holter condition.

53. The method of claim 49, wherein the step of identifying at least one abnormal condition further comprises:

identifying at least one abnormal condition relating to an atrial event.

54. The method of claim 49, wherein the step of identifying at least one abnormal condition further comprises:

identifying at least one abnormal condition relating to a ventricle event.

55. The method of claim 49, wherein the step of identifying at least one abnormal condition further comprises:

identifying at least one abnormal condition relating to a pacing event.

56. The method of claim 49, wherein the step of identifying at least one abnormal condition further comprises:

identifying at least one abnormal condition relating to a sensing event.

57. The method of claim 49, wherein the step of identifying the optimal revised implantable medical device setting further comprises:

utilizing an abductive diagnostic reasoning strategy.

58. The method of claim 49, wherein the step of identifying the optimal revised implantable medical device setting further comprises:

evaluating at least one implantable medical device setting.

59. The method of claim 49, wherein the step of identifying the optimal revised implantable medical device setting further comprises:

evaluating information based upon test procedures completed after the step of identifying at least one abnormal behavior associated with the implantable medical device.

60. The method of claim 49, and further comprising:

performing at least one additional diagnosis test; and identifying the optimal revised implantable medical device setting based upon the at least one possible revised implantable medical device setting in conjunction with the at least one additional diagnostic test.

61. A method of providing information to a clinician relating to optimal settings of an implantable medical device for a specific patient, the method comprising:

identifying at least one abnormal condition associated with the implantable medical device;

identifying evidence associated with at least one abnormal behavior;

categorizing the evidence into one of confirmed solution, rejected solution, or suspected solution;

performing addition diagnostics based upon a suspected solution to identify new evidence;

identifying an optimal revised implantable medical device setting based upon a confirmed solution; and displaying the optimal revised implantable medical device setting.

62. The method of claim 61, wherein the step of categorizing the evidence further comprises:

categorizing the evidence into the confirmed solution if the identified evidence confirms a previous solution.

63. The method of claim 61, wherein the step of categorizing the evidence further comprises:

categorizing the evidence into the rejected solution if the identified evidence proves a previous solution false.

64. The method of claim 61, wherein the step of categorizing the evidence further comprises:

categorizing the evidence into the suspected solution if the identified evidence indicates that additional testing should be performed to further categorize the evidence.

* * * * *